(12) United States Patent
Huang et al.

(10) Patent No.: US 8,911,687 B2
(45) Date of Patent: Dec. 16, 2014

(54) MINIATURE SIEVE APPARATUS AND MANUFACTURING METHOD THEREOF

(75) Inventors: Chun-ming Huang, Hsinchu (TW);
Chen-chia Chen, Hsinchu (TW);
Chi-sheng Lin, Hsinchu (TW);
Chien-ming Wu, Hsinchu (TW)

(73) Assignee: National Applied Research Laboratories, Hsinchu (TW)

( * ) Notice: Subject to any disclaimer, the term of this patent is extended or adjusted under 35 U.S.C. 154(b) by 52 days.

(21) Appl. No.: 13/547,072

(22) Filed: Jul. 12, 2012

(65) Prior Publication Data

US 2013/0259772 A1    Oct. 3, 2013

(30) Foreign Application Priority Data

Apr. 2, 2012   (TW) .............................. 101111756 A

(51) Int. Cl.
*B01D 35/00* (2006.01)
*B01D 41/00* (2006.01)
*B01D 29/07* (2006.01)

(52) U.S. Cl.
USPC ........... 422/534; 210/203; 210/295; 210/314; 210/499; 210/500.26

(58) Field of Classification Search
USPC ................................................. 209/247, 250
See application file for complete search history.

(56) References Cited

U.S. PATENT DOCUMENTS

| 2,136,170 | A | * | 11/1938 | Luertzing | ....................... 210/94 |
| 4,542,518 | A | | 9/1985 | Anthony | |
| 7,846,743 | B2 | | 12/2010 | Tai et al. | |
| 2004/0079696 | A1 | * | 4/2004 | Hernandez | ..................... 210/435 |
| 2007/0025883 | A1 | * | 2/2007 | Tai et al. | ...................... 422/101 |
| 2009/0101559 | A1 | | 4/2009 | Bala Subramaniam et al. | |
| 2009/0188864 | A1 | * | 7/2009 | Zheng et al. | .................. 210/641 |

FOREIGN PATENT DOCUMENTS

| TW | 201116308 A | 5/2011 |
| TW | 201119726 A | 6/2011 |

OTHER PUBLICATIONS

Goran Stemme et al., "A Sub-micron Particle Filter in Silicon", 1990, Sensors and actuators. A. Physical. Volume and ISsue No. 23, pp. 904-907.*
X. Yang, J. M. Yang, Y. C. Tai, C. M. Ho, "Micromachined membrane particle filters", Sensors and Actuators 73 (1999) 184-191.
B. Lu, S. Zheng, B. Q. Quach, Y. C. Tai, "A Study of the Autofluorescence of Parylene Materials for µTAS Applications", Lab on a Chip, 10 (2010) 1826-1834.

* cited by examiner

*Primary Examiner* — Jill Warden
*Assistant Examiner* — Julie Tavares
(74) *Attorney, Agent, or Firm* — Mark M. Friedman

(57) ABSTRACT

A miniature sieve apparatus is described and includes a first sieve, a separator and a second sieve from top to bottom. The first and second sieves are formed with at least one first mesh and a plurality of second meshes, respectively. The first and second meshes are misaligned with each other in a vertical direction of the first and second sieves. The miniature sieve apparatus is provided to separate or screen microparticles with different sizes, such as target cells, bio-medical particles, organic or inorganic microparticles. Additionally, the invention also provides a manufacturing method of the miniature sieve apparatus, and the same material is applied to manufacture the sieves and the separators. Thus, the problem caused by the residual thermal stress due to different material can be solved. Therefore, the cost of the miniature sieve apparatus can be lowered as the yield rate thereof is improved.

3 Claims, 8 Drawing Sheets

MINIATURE SIEVE APPARATUS AND MANUFACTURING METHOD THEREOF

FIELD OF THE INVENTION

The present invention relates to a miniature sieve apparatus and a manufacturing method thereof, and more particularly to a miniature sieve apparatus for separating target cells, biomedical particles, organic or inorganic microparticles with different sizes and a manufacturing method thereof.

BACKGROUND OF THE INVENTION

Traditionally, cell separation technologies include active and passive cell separation technologies, wherein the active cell separation technology means that the target cells are filtrated or separated by different approaches, such as dielectrophoresis, optical tweezers, and magnetic force. Furthermore, most of the passive cell separation technologies mean that the target cells are filtrated or separated by sieve elements, and the size of meshes on sieves can prevent target cells from passing through the sieves.

For example, referring now to Taiwan Pat. No. I308131, a bio-particle capturing apparatus having a 3D structure and a manufacturing method thereof are disclosed, wherein the capturing apparatus is a trap to capture bio-particles to the predetermined wells by dielectrophoresis (DEP) force. The characteristic of the capturing apparatus is to apply a 3D-structural concept to a dielectrophoresis biochip which is mainly used to trap and immobilize bio-particles, such as cells, functional latex beads, nano-particles or gene segments.

As described in the Taiwan Pat. No. I308131, the bio-particles capturing apparatus having the 3D structure comprises an upper layer, microfluidic channels and a lower layer, wherein the upper layer is formed with an upper electrode, an inlet and an outlet; and the lower layer is formed with a lower electrode. A sample fluid can flow from the inlet into the capturing apparatus, flow through the microfluidic channels, and then flow out of the outlet of the capturing apparatus. Furthermore, the outlet is formed with matrix-type wells. The major characteristic of the capturing apparatus is that the directions of electric fields generated by the electrodes of the upper and lower layers are vertical to the flow direction of the sample fluid of the microfluidic channels, so as to form uneven longitudinal electric fields. Thus, the bio-particles in the microfluidic channels can be rapidly captured into the predetermined wells of the low layer.

However, the bio-particle capturing apparatus having the 3D structure is a trapping device which uses the DEP force generated by the electrode to trap the bio-particles into the predetermined wells. In actual use, a buffer with lower conductivity (~570 µS/cm) must be applied to the capturing apparatus for trapping or separating the bio-particles. For example, the conductivity of human blood is about 0.1~2 S/cm, and thus does not meet the condition of buffer with the lower conductivity for the trapping or separating the bio-particles by using DEP force. Consequently, before the cell separation, it needs to firstly separate the cells of blood by the method of density gradient separation. After centrifugation, the collected cells are added into the lower conductivity buffer, so that the more powerful DEP force can be generated to trap the target cells.

As described above, except for actively trapping the target cells of blood samples by the DEP force, magnetic particles also can be immobilized on cell membrane, or the magnetic particles can be introduced into the cells by uptake events, so target cells can be separated by manipulated magnetic force. However, most of the biological features of tumor cells are almost the same as that of health cells. Therefore, it is necessary to screen a high specific protein for particular membrane protein of particular cells at first, conjugate the magnetic particles to the specific protein, and then to apply the property of the specific protein able to identify the particular membrane protein of the particular cells for immobilizing the magnetic particles onto the cell surface of particular tumor cells as to-be-screened targets. Moreover, if using the method of inducing the particular cells to actively take into the magnetic particles as to-be-screened targets, a particular structural molecule must be modified on the surface of the magnetic particles, so that the specific cells are promoted to swallow them. However, no matter for modifying the surface of the magnetic particles or conjugating the magnetic particles to the specific protein, the particular magnetic particles must be added during screening different target cells, so that the cost of detection will be increased.

Besides, the easier and more convenient method of separating the bio-particles is to use a sieve apparatus to the passive separation of bio-particles. That is, the size of the meshes defined on the sieve apparatus can be used to screen bio-particles with different diameters in a sample fluid. It is unnecessary to execute any pre-treating steps before passively screening the sample fluid, the time cost of screening or separating the target bio-particles can be relatively decreased, and the manufacture cost of the sieves can be lowered by mass production of the sieves.

Recently, 2D or 3D sieve apparatus made by micro-electromechanical systems (MEMS) technology are widely applied to separate cells, wherein the meshes of the sieve are used to trap white blood cells of blood; and red blood cells, platelets and serum of blood can pass through the meshes of the sieves, so as to carry out the purpose of screening and separating the white blood cells. However, in fact, for a sieve apparatus made of silicon nitrite or parylene C and processed by MEMS technology, during forming the 3D sieve structure, a sacrificial layer must be sandwiched between an upper sieve and a lower sieve. The sacrificial layer is selectively etched after forming upper meshes on the upper sieve. Therefore, the process of the 3D sieve apparatus must consider the ratio of the etching rate between materials of the upper sieve, the lower sieve and the sacrificed layer. Moreover, it also needs to consider the three materials of the 3D sieve apparatus with the problems of residual stress generated during the manufacture process and to consider relative parameters thereof, so that it is significantly difficult in the whole manufacturing process of the 3D sieve apparatus.

As a result, the traditional sieve apparatus manufactured, by the MEMS technology is not only complicated and difficult to execute MEMS processes, but also the stability of the manufacture yield thereof is still not good. Therefore, it is difficult to lower the manufacture cost of industrial mass production. Therefore, it is necessary to provide a miniature sieve apparatus and a manufacturing method thereof to solve the problems existing in the conventional sieve apparatus, as described above.

SUMMARY OF THE INVENTION

A primary object of the present invention is to provide a miniature sieve apparatus, wherein the same material (such as silicon substrate) is used to manufacture a first and a second sieve, and a separator is disposed between the first and second sieves, wherein the material of the separator can be made of the same or different material of the first and second sieves. Because it is unnecessary for the above-mentioned process to use coating steps, the problems of generating residual stress and stress distribution in the traditional three-dimensional sieve can be improved, and the structural stability of the miniature sieve apparatus can be enhanced.

A secondary object of the present invention is to provide a manufacturing method of a miniature sieve apparatus, wherein material of a sacrificial layer is not used between the first and second sieves, and the first and second sieves can be formed with a first and a plurality of second meshes by etching, respectively. Therefore, it is simple to precisely control the mesh size of the sieves. Further, when manufacturing another miniature sieve apparatus of different specification for screening different targets, it only needs to change new first sieve with different mesh size, so that the design flexibility can be increased, the manufacture process can be simplified, and the manufacture efficiency of the miniature sieve apparatus can be enhanced.

To achieve the above object, the present invention provides a miniature sieve apparatus which comprises at least one sieve unit, and each of the sieve unit comprises a first sieve, a separator and a second sieve. The first sieve is formed with at least one first mesh; the separator is stacked on one side of the first sieve and formed with a separation hole; and the second sieve is stacked on the other side of the separator, and the second sieve is formed with a plurality of second meshes, wherein the diameter of the second meshes is smaller than that of the first mesh, and the first and second sieve are made of the same material.

In one embodiment of the present invention, the miniature sieve comprises a plurality of the sieve units, and the first sieves, the separators and the second sieves of all of the sieve units are integrated into one plate, respectively.

In one embodiment of the present invention, the first mesh and the second meshes are misaligned with each other in a vertical direction of the first and second sieves.

In one embodiment of the present invention, the material of the first and second sieves are simultaneously selected from Si, SiC or glass; the material of the separator is selected from Si, SiC, glass, photoresist, polyimide or cyclic olefin copolymer (COC).

In one embodiment of the present invention, the material of the separator is selected from the same material of the first and second sieves. Thus, during assembling, the miniature sieve apparatus can provide the same coefficient of thermal expansion (CTE) for maintaining planarity after assembling and enhancing the fabrication yield.

In one embodiment of the present invention, the miniature sieve is further provided with a container and a pumping/injecting device for a sample fluid to pass through the first sieve, the separator and the second sieve in turn.

Moreover, the present invention provides a manufacturing method of a miniature sieve apparatus, which comprises steps of: forming a first sieve and a second sieve, respectively or simultaneously, wherein the first sieve is formed with at least one first mesh and the second sieve is formed with a plurality of second meshes, the diameter of the second meshes is smaller than that of the first mesh, and the first sieve and the second sieve are made of the same material; coating a photoresist on the second sieve, and defining a separation hole on the photoresist by standard photolithography, so as to form a separator; and stacking the first sieve on the separator to construct a miniature sieve.

Furthermore, the present invention also provides a manufacturing method of a miniature sieve apparatus, which comprises steps of: forming a first sieve, a separator and a second sieve, respectively or simultaneously, wherein the first sieve is formed with at least one first mesh, the separator is formed with a separation hole, and the second sieve is formed with a plurality of second meshes, the diameter of the second meshes is smaller than that of the first mesh, and the first sieve and the second sieve are made of the same material; and stacking the first sieve, the separator and the second sieve from top to bottom, to construct a miniature sieve apparatus.

In one embodiment of the present invention, the first mesh and the second meshes are misaligned with each other in a vertical direction of the first and second sieves.

According to the design concept of the present invention, when the to-be-sieved targets are changed, it only needs to change new first sieve with different mesh size, so as to construct a new miniature sieve having corresponding specification after heating assembly. Therefore, the manufacturing processes of the miniature sieve apparatus can be simplified and the cost thereof can be lowered, while the industrial requirement of re-design flexibility can be satisfied. Furthermore, the diversity of the miniature sieve apparatus can be increased to meet needs of the market.

DETAILED DESCRIPTION OF THE PREFERRED EMBODIMENTS

The structure and the technical means adopted by the present invention to achieve the above and other objects can be best understood by referring to the following detailed description of the preferred embodiments and the accompanying drawings. Furthermore, directional terms described by the present invention, such as upper, lower, front, back, left, right, inner, outer, side, longitudinal/vertical, transverse/horizontal, and etc., are only directions by referring to the accompanying drawings, and thus the used directional terms are used to describe and understand the present invention, but the present invention is not limited thereto.

Figure 1:
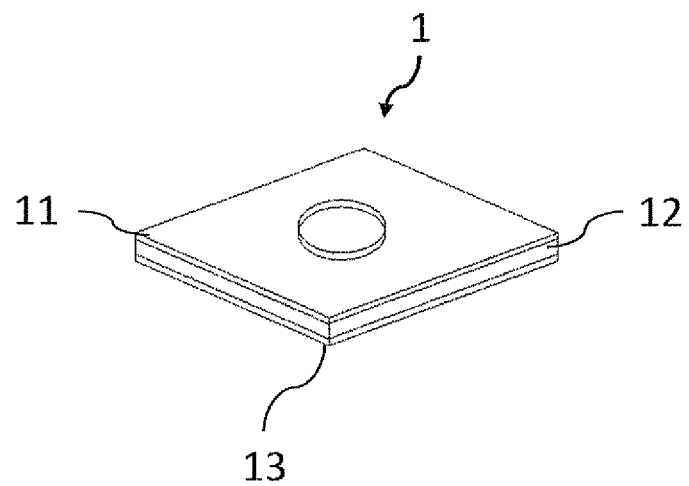
FIG. 1 is an assembled view of a sieve unit of a miniature sieve apparatus according to a first embodiment of the present invention.
Figure 2:
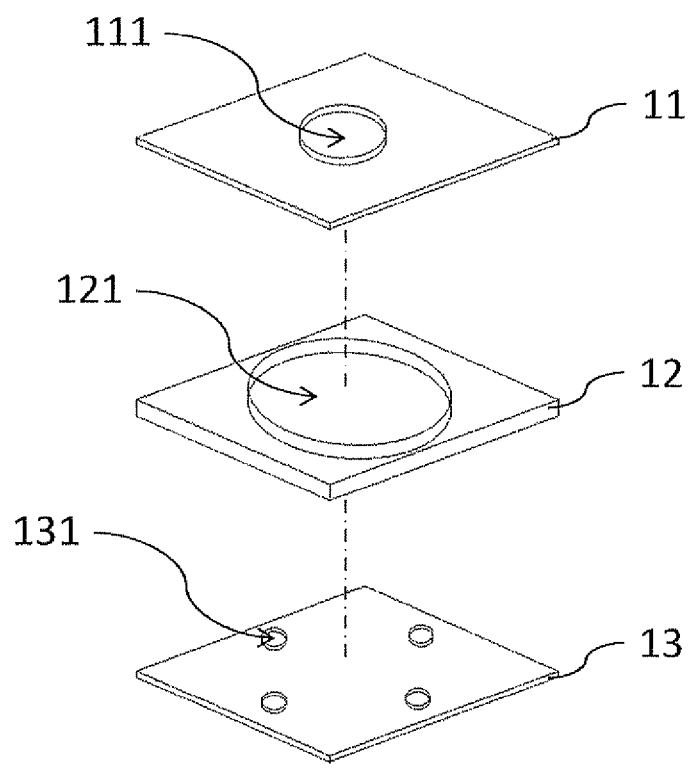
FIG. 2 is an exploded view of the sieve unit of the miniature sieve according to the first embodiment of the present invention.

Referring now to FIGS. 1 and 2, a miniature sieve apparatus according to a first embodiment of the present invention is illustrated. As shown, the miniature sieve designated by numeral 1 comprises at least one sieve unit 1 and each of the sieve unit 1 comprises a first sieve 11, a separator 12 and a second sieve 13. The first sieve ills formed with at least one first mesh 111. The separator 12 is stacked on one side of the first sieve 11 and formed with a separation hole 121. The second sieve 13 is stacked on the other side of the separator 12, wherein the second sieve 13 is formed with a plurality of second meshes 131. The diameter of the second meshes 131 is smaller than that of the first mesh 111, and the diameter of the second meshes 131 and the first mesh 111 are smaller than that of the separation hole 121.

Furthermore, the first and second sieves 11,13 are selected from plates of the same material. For example, the material of the first and second sieves 11,13 can be selected from silicon (Si), silicon carbide (SiC) or glass, simultaneously. Moreover, the material of the separator 12 is selected from silicon (Si), silicon carbide (SiC), glass, photoresist (such as SU-8), polyimide or cyclic olefin copolymer (COC). Particularly, the material of the separator 12 is selected from the same material of the first and second sieves 11,13. Thus, during assembling, the first sieve 11, the separator 12 and the second sieve 13 of the miniature sieve apparatus can provide the same coefficient of thermal expansion (CTE) for maintaining planarity after assembling and enhancing the fabrication yield.

Figure 3:
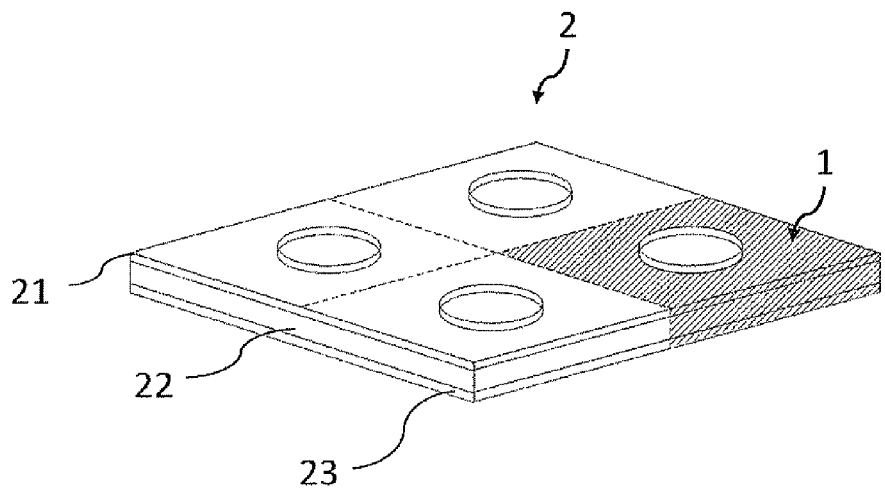
FIG. 3 is an assembled view of the miniature sieve according to the first embodiment of the present invention.
Figure 4:
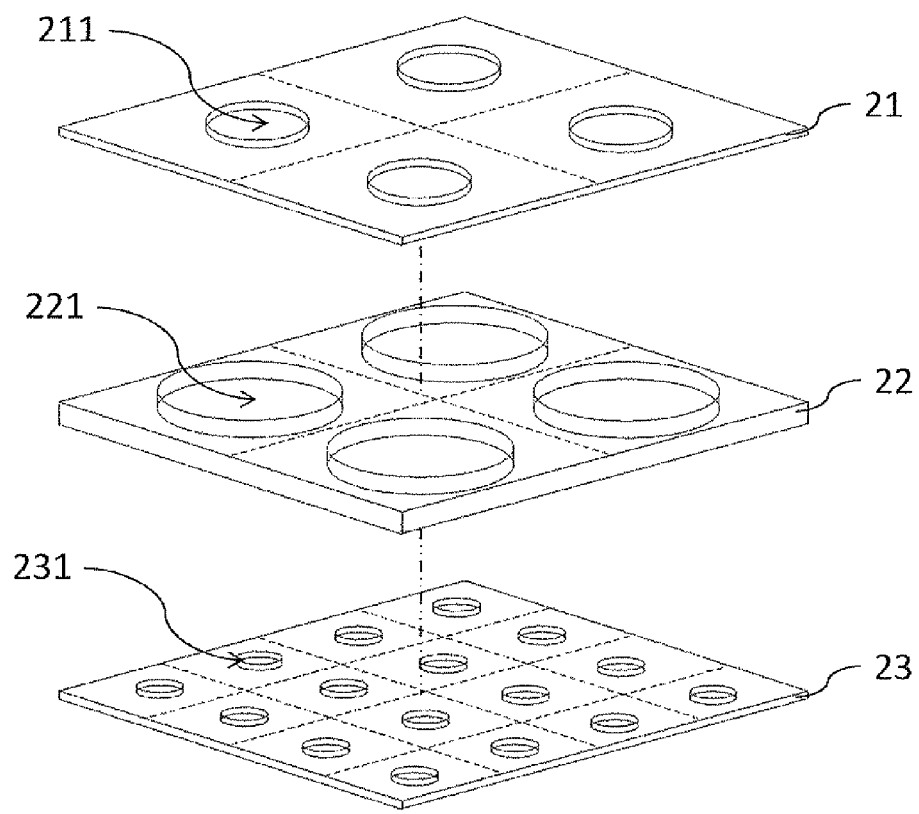
FIG. 4 is an exploded view of the miniature sieve according to the first embodiment of the present invention.

Referring to FIGS. 3 and 4, in the first embodiment of the present invention, the miniature sieve apparatus designated by numeral 2 is exemplified to comprise a plurality of the sieve units 1, such as having four sieve units 1 in a matrix arrangement, but the number of the sieve units 1 is not limited thereto, wherein the number of the sieve units 1 also can be two, three, five or more. Moreover, in the same the miniature sieve apparatus 2, the first sieves 21 of all of the sieve units 1 are integrated into a first plate, the separator 22 of all of the sieve units 1 are integrated into a second plate, and the second sieves 23 of all of the sieve units 1 are integrated into a third plate, and the three plates can be assembled to construct the miniature sieve apparatus 2. Furthermore, the first mesh 211 and the second meshes 231 are misaligned with each other in a vertical direction of the first 21 and second sieves 23, i.e. the first meshes 211 are completely misaligned with the second meshes 231 in the vertical direction, or the first meshes 211 are partially aligned with the second meshes 231.

In the first embodiment, the present invention provides a manufacturing method of the miniature sieve apparatus 2, which comprises steps of: forming a first sieve 21 and a second sieve 23, respectively or simultaneously, wherein the first sieve 21 is formed with at least one first mesh 211 and the second sieve 23 is formed with a plurality of second meshes 231, the diameter of the second meshes 231 is smaller than that of the first mesh 211, and the first sieve 21 and the second sieve 23 are made of plates of the same material (such as silicon substrate). Then, coating a photoresist (such as SU-8) on the second sieve 23, and defining a separation hole 221 on the photoresist by exposing and developing, so as to form a separator 22; and then stacking the first sieve 21 on the separator 22 to construct a miniature sieve apparatus 2.

Alternatively, in another embodiment, the manufacturing method of the miniature sieve apparatus 2 of the present invention can comprise steps of: forming a first sieve 21, a separator 22 and a second sieve 23, respectively or simultaneously, wherein the first sieve 21 is formed with at least one first mesh 211, the separator 22 is formed with a separation hole 221, and the second sieve 23 is formed with a plurality of second meshes 231, wherein the diameter of the second meshes 231 is smaller than that of the first mesh 211, and the first sieve 21 and the second sieve 22 are made of plates of the same material (such as silicon substrate). Then, to stack the first sieve 21, the separator 22 and the second sieve 23 from top to bottom, to construct a miniature sieve apparatus 2.

Figure 5:
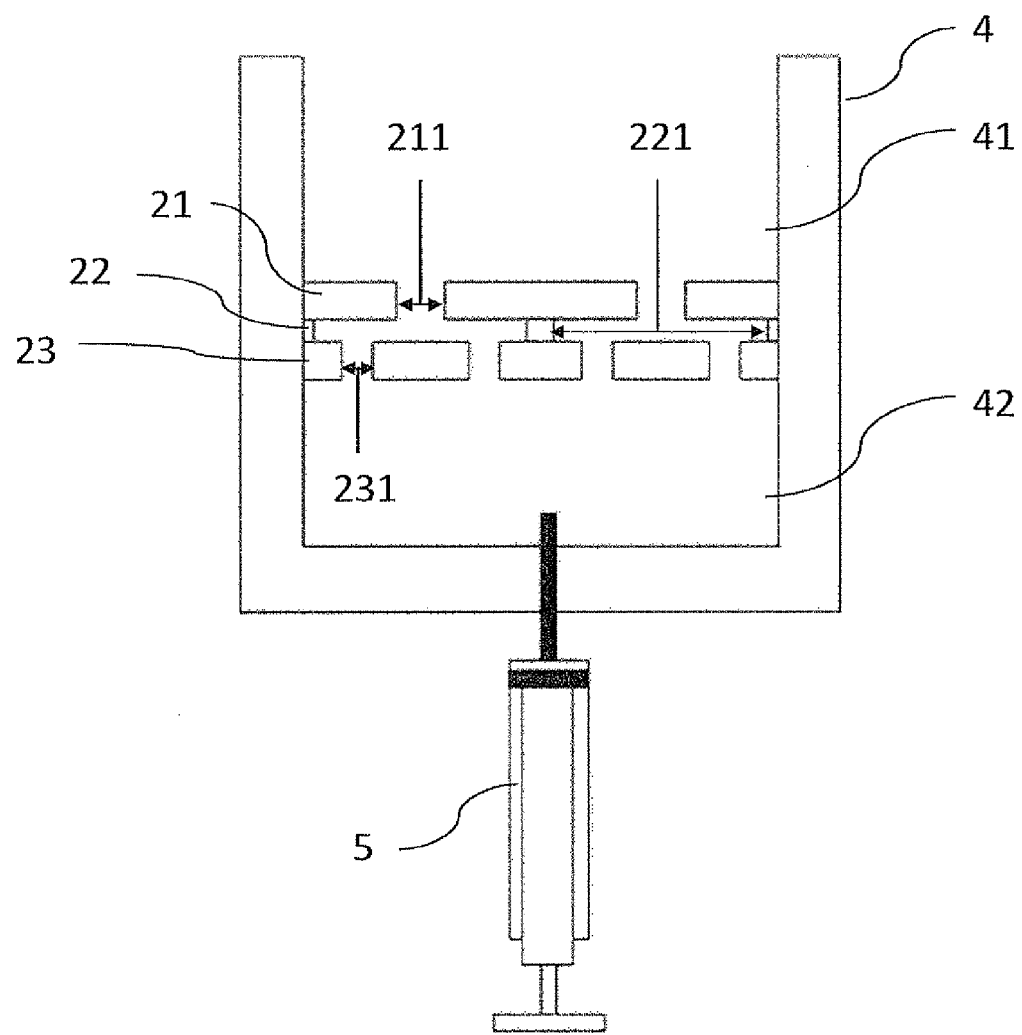
FIG. 5 is an assembled cross-sectional view of the miniature sieve with a container and a pumping/injecting device according to the first embodiment of the present invention.
Figure 6:
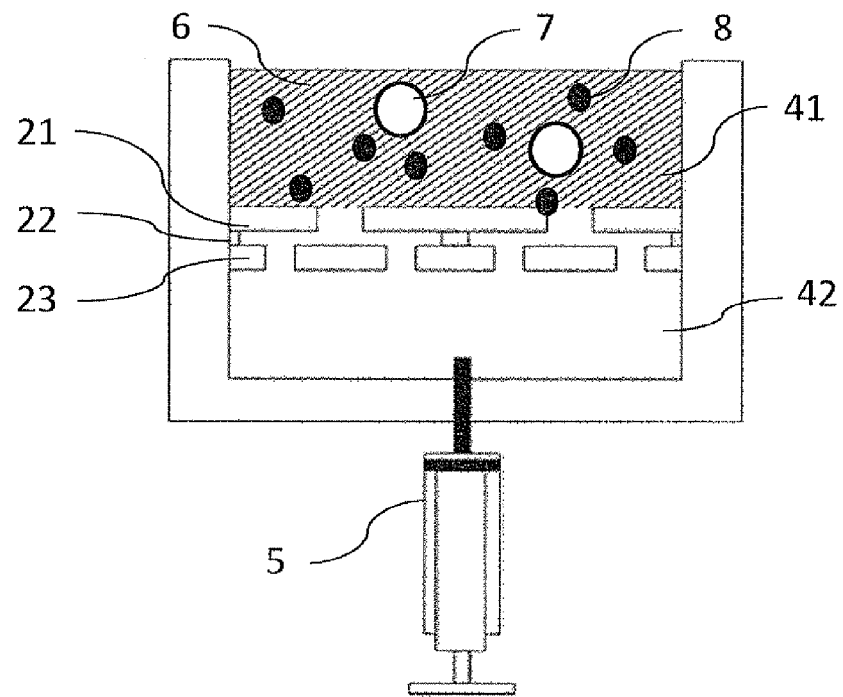
FIG. 6 is an operational view of the sieve unit of the miniature sieve before sieving according to the first embodiment of the present invention.
Figure 7:
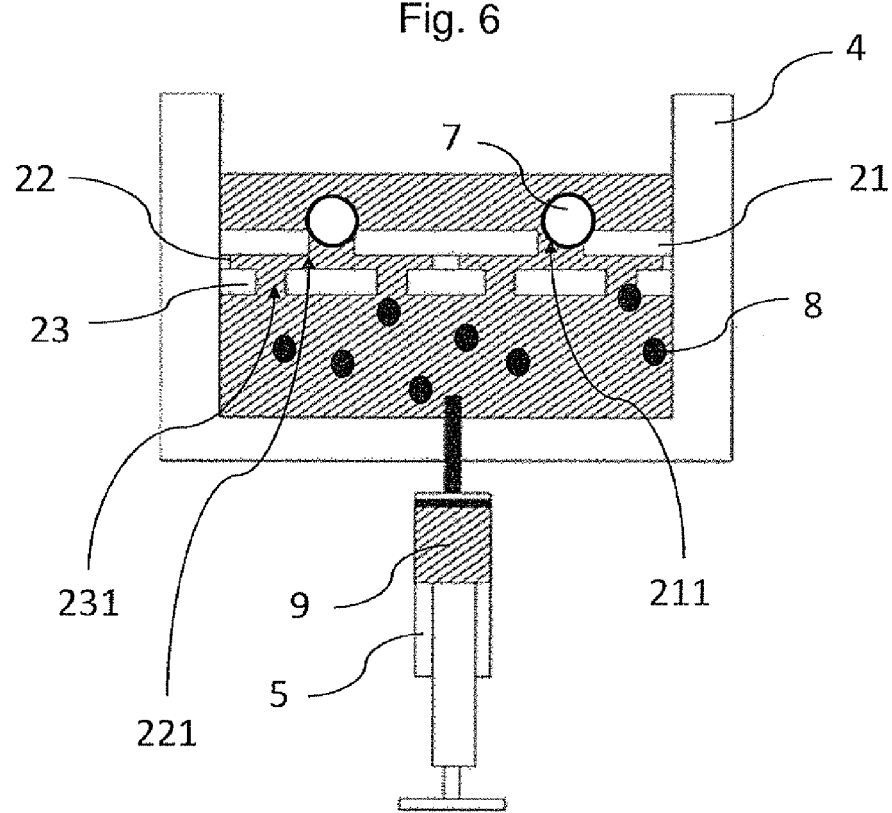
FIG. 7 is an operational view of the sieve unit of the miniature sieve after sieving according to the first embodiment of the present invention.
Figure 8:
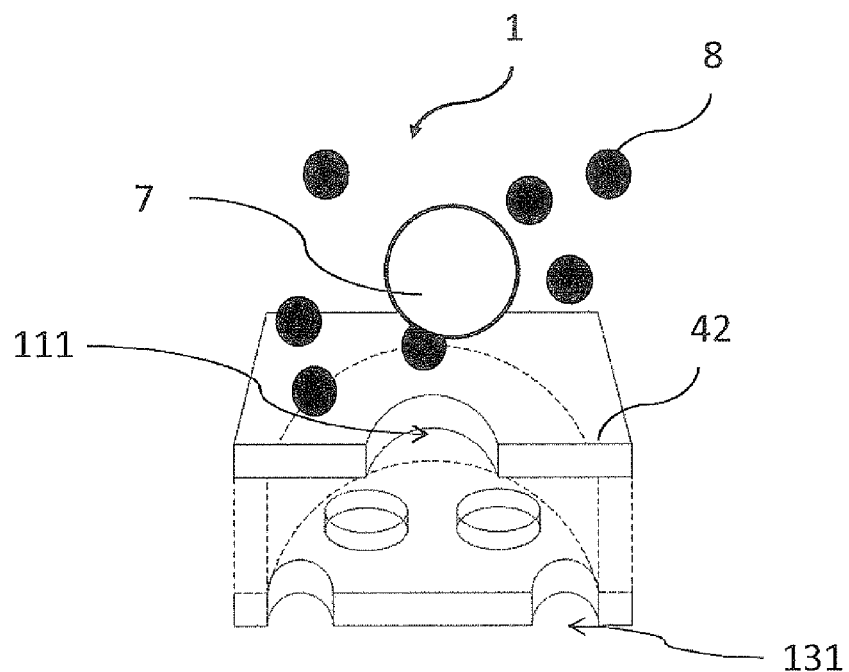
FIG. 8 is a perspective and partially cross-sectional view of the sieve unit in FIG. 6.
Figure 9:
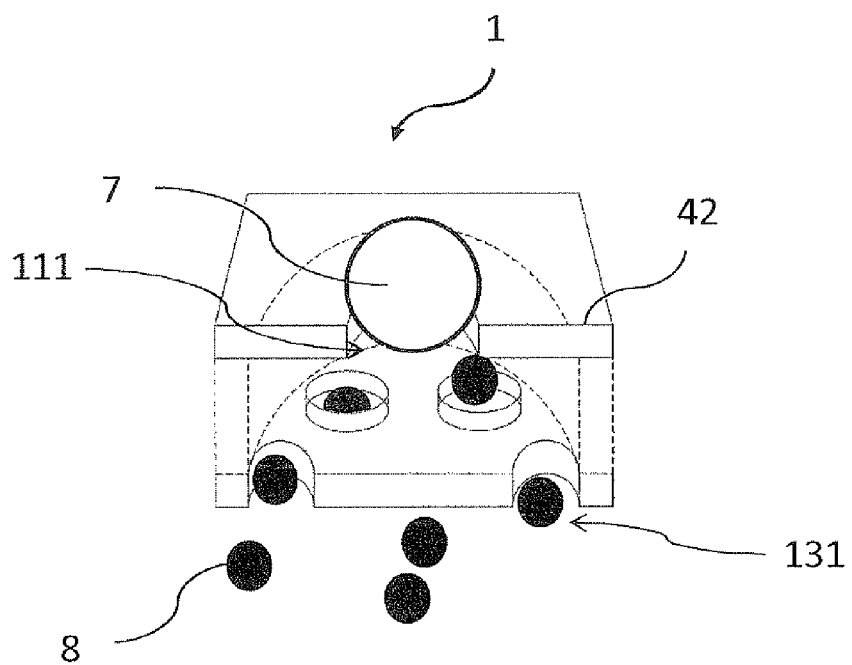
FIG. 9 is a perspective and partially cross-sectional view of the sieve unit in FIG. 7.

Referring to FIG. 5, in the first embodiment of the present invention, the miniature sieve 2 (as shown in FIG. 3) is further provided with a container 4 and a pumping/injecting device 5, wherein the miniature sieve apparatus 2 is fixed into the container 4 to separate an inner space of the container 4 into a first chamber 41 and a second chamber 42 from top to bottom.

Next, referring to FIGS. 6, 7, 8 and 9, as a sample fluid 6 (such as blood) is loaded to the first chamber 41, the sample fluid 6 passes through the first meshes 211, the separation holds 221 and the second meshes 231 in turn, for screening or separating first microparticles (such as white blood cells) and second microparticles (such as red blood cells). The pumping/injecting device 5 is installed on the side of the second chamber 42, and provides a pumping/drawing function. When the pumping/injecting device 5 pumps, the sample fluid 6 is accelerated to flow from the first chamber 41 to the second chamber 42. In another embodiment of the present invention, the pumping/injecting device 5 also can be installed on the side of the first chamber 41 to provide an injecting/pressurizing function to accelerate the sample fluid 6 to pass the first chamber 41 through the second chamber 42.

It should be noted that the sizes of the first and second meshes 211,231 of the present invention can be designed to be smaller than the size of the first microparticles 7, and larger than the size of the second microparticles 8. Meanwhile, the diameter of the second meshes 231 is smaller than that of the first meshes 211. Therefore, during sieving, the second microparticles 8 of the sample fluid 6 passes through a pathway defined by the first meshes 211, the separation holes 221 and the second meshes 231 in turn. The sample fluid 6 passes through the second meshes 231 to become a filtrate 9 which then flows into the second chamber 42 and/or the pumping/injecting device 5. And, one portion of the first microparticles 7 is inserted into and engaged with the first meshes 211. Thus, the present invention can carry out the purpose of screening or separating the first and second microparticles 7,8.

Figure 10:
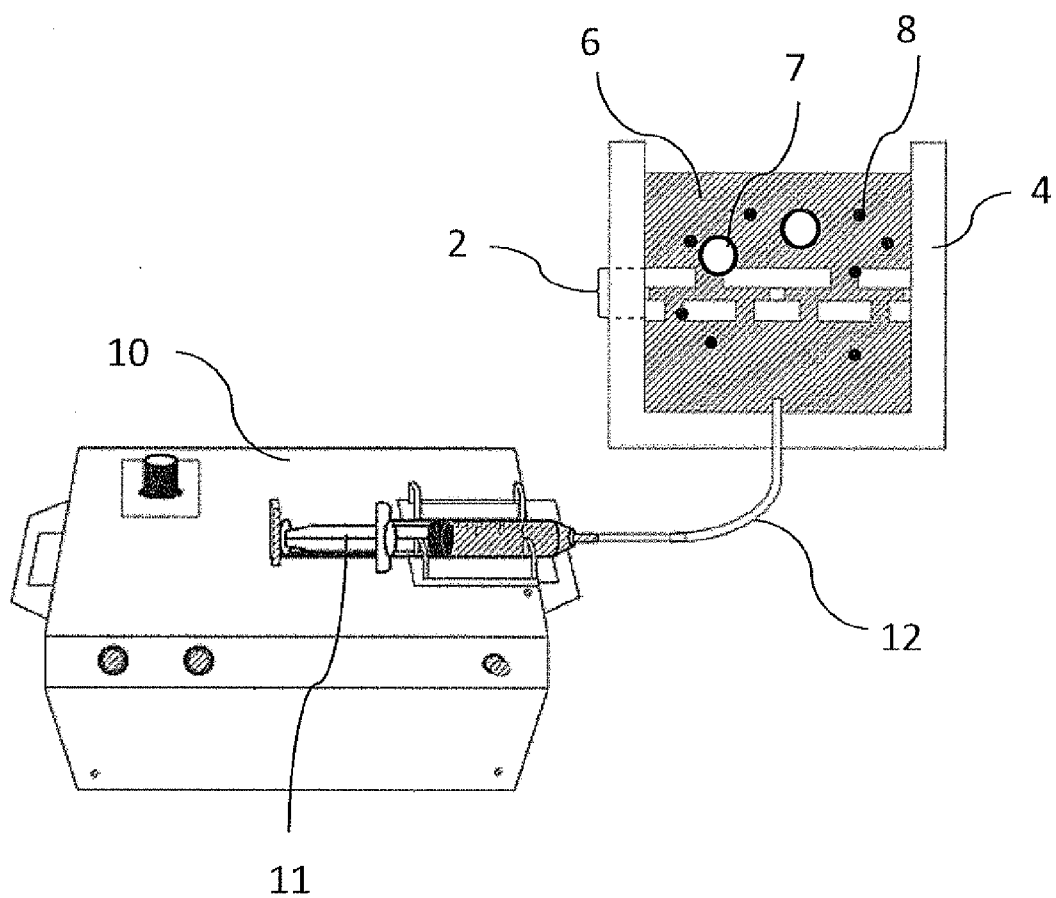
FIG. 10 is an application view of the miniature sieve according to the first embodiment of the present invention.

Referring to FIG. 10, in the first embodiment of the present invention, the miniature sieve is also provided with an auto-pumping/injecting device 10 which comprises a pumping/injecting device 11 and a tube 12, wherein the pumping/injecting device 11 is installed on the auto-pumping/injecting device 10, and has a front end connected to the container 4 of the miniature sieve apparatus 2 through the tube 12, in order to screen or separate the first microparticles 7 within a predetermined period. The pumping/injecting device 11 is substantially the same as the foregoing pumping/injecting device 5, and installed on the side of the second chamber 42 for providing pumping/drawing function. Alternatively, the pumping/injecting device 11 also can be installed on the side of the first chamber 41 for providing injecting/pressurizing function.

Figure 11:
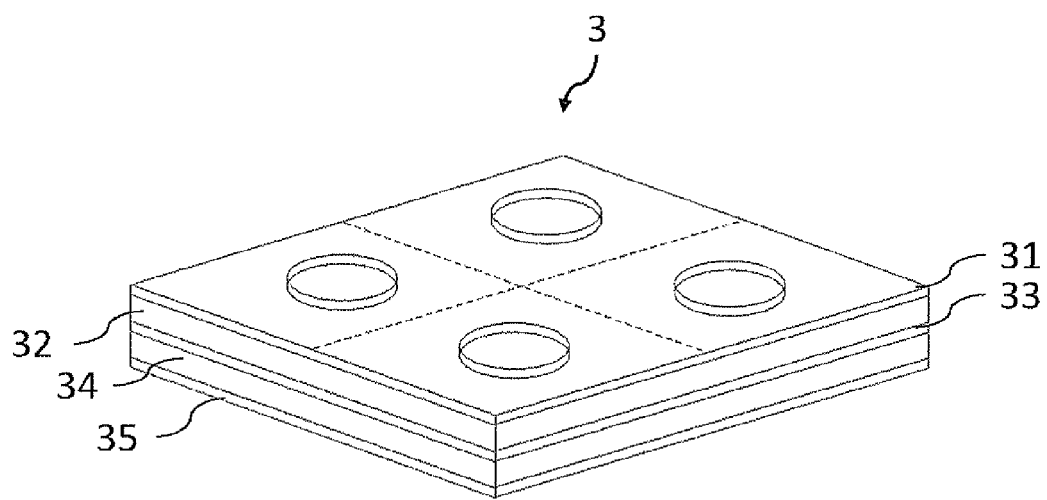
FIG. 11 is an assembled view of the miniature sieve according to the second embodiment of the present invention.
Figure 12:
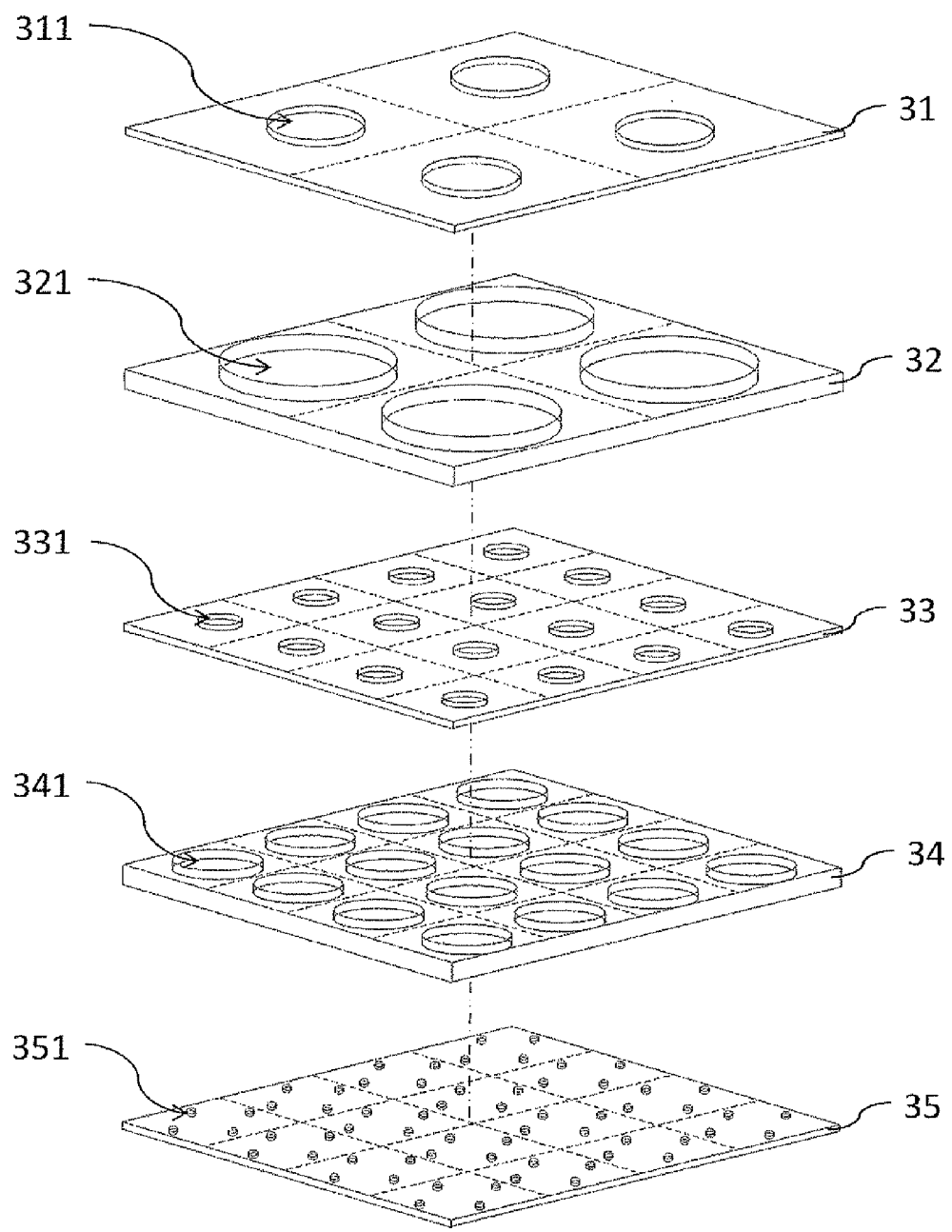
FIG. 12 is an exploded view of the miniature sieve according to the second embodiment of the present invention.

Furthermore, referring to FIGS. 11 and 12, in the second embodiment of the present invention, the miniature sieve apparatus 3 is similar to the miniature sieve apparatus 2 of the first embodiment of the present invention, but the miniature sieve apparatus 3 of the second embodiment comprises a first sieve 31, a first separator 32, a second sieve 33, a second separator 34 and a third sieve 35. The first sieve 31 is formed with a plurality of first meshes 311. The first separator 32 is stacked on one side of the first sieve 31 and formed with a plurality of first separation holes 321. The second sieve 33 is stacked on the other side of the first separator 32 and formed with a plurality of second meshes 331. The second separator 34 is stacked on the other side of the second sieve 33 and formed with a plurality of second separation holes 341. The third sieve 34 is stacked on the other side of the second separator 34 and formed with a plurality of third meshes 351. Furthermore, the diameter of the third meshes 351 is smaller than that of the second meshes 331 and smaller than that of the first meshes 311. Additionally, the first, second and third meshes 311,331 are misaligned with each other in a vertical direction of the first, second sieves 31,33. And, the second and third meshes 331,351 are also misaligned with each other in a vertical direction of the second and third sieves 33,35.

It should be noted that the size of the first meshes 211 of the present invention is designed to be smaller than that of the first microparticles 7, but larger than that of the second microparticles 8. Therefore, during screening, the sample fluid 6 carries the second microparticles 8 and passes through the pathway defined by the first meshes 211, the separation holes 221 and the second meshes 231. The sample fluid 6 passes through the second meshes 231 to become a filtrate 9 which then flows into the second chamber 42 and/or the pumping/injecting device 5. Finally, a portion of the first microparticles 7 is inserted into and engaged with the first meshes 211. Thus, the present invention can carry out the purpose of screening or separating the first and second microparticles 7,8.

As described above, the first and second sieves 21,23 of the present invention are made of plates of the same material (such as silicon substrate), and the separator 22 is disposed between the first and second sieves 21,23, wherein the material of the separator 22 is preferably, but not limited to, made of the same material of the first and second sieves 21,23. It is unnecessary for the manufacturing process to use steps of coating and heating, so that the problems of generating residual stress and residual stress distribution in the traditional three-dimensional sieve can be improved, and the structural stability of the miniature sieve apparatus 2 can be enhanced. Furthermore, material of a sacrificial layer is not used between the first and second sieves 21,23 and the first and second sieves 21,23 can be etched to form meshes, respectively. Therefore, it is simple to control the manufacture precision of the size of the meshes. When manufacturing another miniature sieve apparatus 2 of different specification for screening different microparticles, it only needs to change new first sieve 21 with different mesh 211, so that the design flexibility can be increased, the manufacture process can be simplified, and the manufacture efficiency of the miniature sieves apparatus 2 can be enhanced.

The present invention has been described with a preferred embodiment thereof and it is understood that many changes and modifications to the described embodiment can be carried out without departing from the scope and the spirit of the invention that is intended to be limited only by the appended claims.

What is claimed is:

1. A miniature sieve, comprising:
    a first plate having a plurality of first sieves that are regularly arranged in a matrix, wherein each of the first sieves has at least one first mesh;
    a second plate stacked on a side of the first plate and having a plurality of separators that are regularly arranged in a matrix, wherein the separators are aligned with the first sieves, respectively, and each of the separators has a separation hole;
    a third plate stacked on a side of the second plate opposite to the first plate and having a plurality of second sieves that are regularly arranged in a matrix, wherein each of the plurality of second sieves has a plurality of second meshes, such that the number of second meshes in the plurality of second sieves is greater than the number of first meshes in the plurality of first sieves, wherein the second sieves are aligned with the separators, respectively, so that a sieve unit is formed by one of the plurality of first sieves along with one of the corresponding separators and one of the plurality of second sieves such that the miniature sieve has a plurality of sieve units; wherein the at least one first mesh in each of the plurality of first sieves and the plurality of second meshes in each of the plurality of second sieves are misaligned with each other in a vertical direction of the aligned first and second sieves; the diameter of the plurality of second meshes is smaller than that of the first mesh.

2. The miniature sieve according to claim 1, wherein the miniature sieve is further provided with a container and a pumping/injecting device for a sample liquid to pass through the first sieve, the separator and the second sieve in turn.

3. The miniature sieve according to claim 1, wherein the first and second sieves are selected from the group consisting of Si and SiC; the separator is selected from the group consisting of Si, SiC, and photoresist.

* * * * *